US012661440B2

(12) United States Patent
Pettersson et al.

(10) Patent No.: US 12,661,440 B2
(45) Date of Patent: Jun. 23, 2026

(54) DIALYSIS SYSTEM HAVING MOTOR DRIVER PRESSURE ESTIMATION OF FLUID WITHIN A PATIENT LINE

(71) Applicants: Vantive US Healthcare LLC, Deerfield, IL (US); Vantive Healthcare GmbH, Glattpark (CH)

(72) Inventors: Michael Pettersson, Malmo (SE); Andreas Winquist, Södra Sandby (SE); Per Andersson, Fureland (SE)

(73) Assignees: Vantive US Healthcare LLC, Deerfield, IL (US); Vantive Healthcare GmbH, Glattpark (CH)

( * ) Notice: Subject to any disclaimer, the term of this patent is extended or adjusted under 35 U.S.C. 154(b) by 287 days.

(21) Appl. No.: 18/539,694

(22) Filed: Dec. 14, 2023

(65) Prior Publication Data

US 2024/0197973 A1 Jun. 20, 2024

Related U.S. Application Data

(60) Provisional application No. 63/432,589, filed on Dec. 14, 2022.

(51) Int. Cl.
A61M 1/28 (2006.01)
A61M 1/16 (2006.01)

(52) U.S. Cl.
CPC .......... A61M 1/282 (2014.02); A61M 1/1613 (2014.02); A61M 1/281 (2014.02); *A61M 2205/3334* (2013.01); *A61M 2205/3341* (2013.01); *A61M 2205/502* (2013.01); *A61M 2205/52* (2013.01)

(58) Field of Classification Search
CPC .... A61M 1/1613; A61M 1/281; A61M 1/282; A61M 2205/3334; A61M 2205/3341; A61M 2205/502; A61M 2205/52
See application file for complete search history.

(56) References Cited

FOREIGN PATENT DOCUMENTS

WO WO 2022/140054 A1 * 6/2022

* cited by examiner

*Primary Examiner* — John Kim
(74) *Attorney, Agent, or Firm* — K&L Gates LLP

(57) ABSTRACT

A dialysis system having motor driven pressure estimation of fluid within a patient line is disclosed. A peritoneal dialysis ("PD") system includes a fluid pump and a patient line that fluidly couples the fluid pump to an indwelling catheter leading into a patient's peritoneal cavity. The PD system also includes a motor driver that controls a motor of the fluid pump and transmits an output signal that is indicative of a load on the motor. The PD system further includes a machine learning algorithm that associates data related to output signals from motor drivers with known fluid pressures within patient lines. A processor of the PD system transmits an input signal to activate the motor driver, receives the output signal from the motor driver, and estimates a fluid pressure within the patient line by applying the data from the received output signal to the machine learning algorithm.

24 Claims, 10 Drawing Sheets

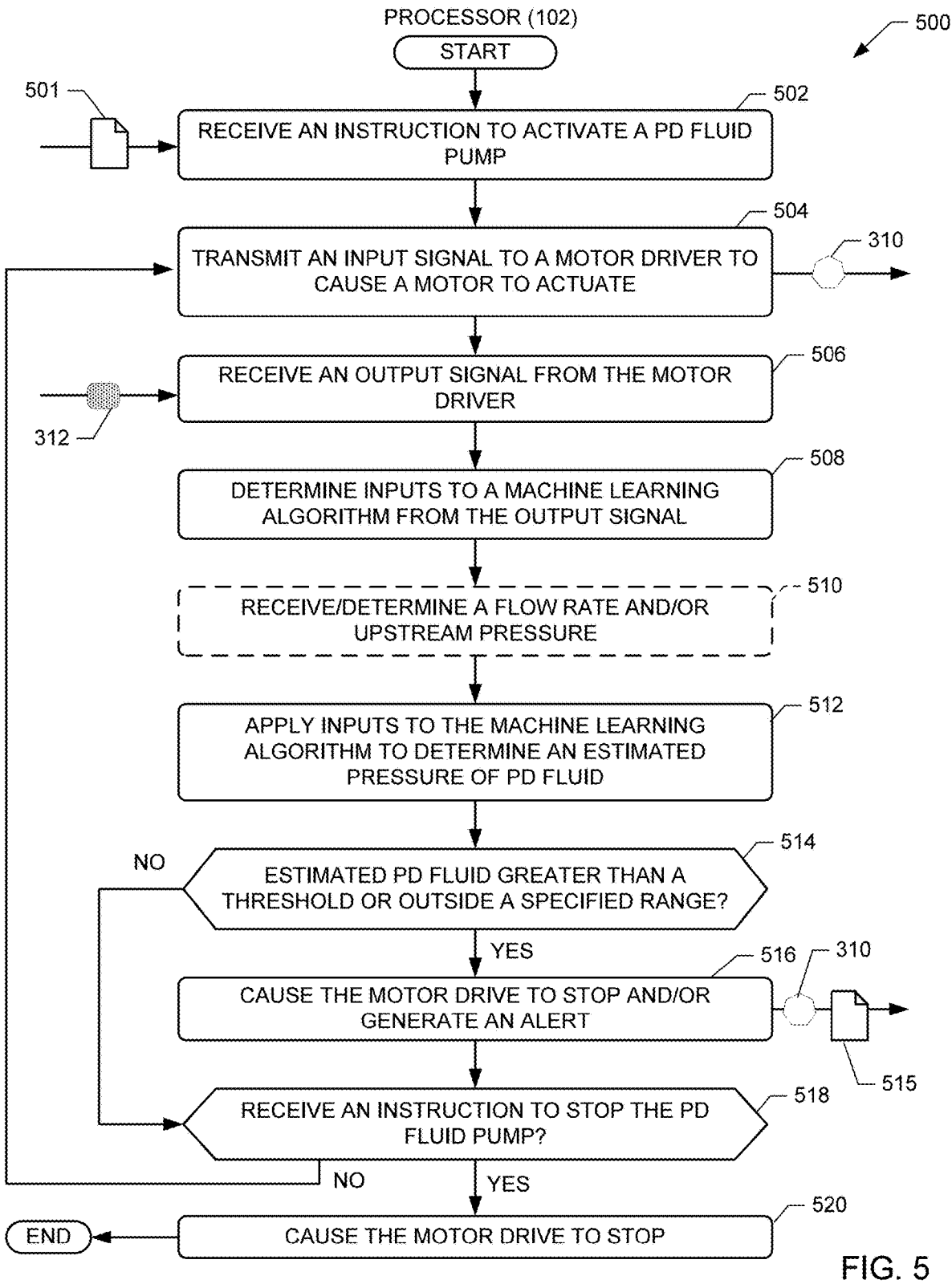

PROCESSOR (102)

START — 500

501

502 — RECEIVE AN INSTRUCTION TO ACTIVATE A PD FLUID PUMP

504 — TRANSMIT AN INPUT SIGNAL TO A MOTOR DRIVER TO CAUSE A MOTOR TO ACTUATE — 310

506 — RECEIVE AN OUTPUT SIGNAL FROM THE MOTOR DRIVER

312

508 — DETERMINE INPUTS TO A MACHINE LEARNING ALGORITHM FROM THE OUTPUT SIGNAL

510 — RECEIVE/DETERMINE A FLOW RATE AND/OR UPSTREAM PRESSURE

512 — APPLY INPUTS TO THE MACHINE LEARNING ALGORITHM TO DETERMINE AN ESTIMATED PRESSURE OF PD FLUID

514 — ESTIMATED PD FLUID GREATER THAN A THRESHOLD OR OUTSIDE A SPECIFIED RANGE?

NO

YES

516 — CAUSE THE MOTOR DRIVE TO STOP AND/OR GENERATE AN ALERT — 310

515

518 — RECEIVE AN INSTRUCTION TO STOP THE PD FLUID PUMP?

NO          YES

520 — CAUSE THE MOTOR DRIVE TO STOP

END

FIG. 5

DIALYSIS SYSTEM HAVING MOTOR DRIVER PRESSURE ESTIMATION OF FLUID WITHIN A PATIENT LINE

PRIORITY CLAIM

This application claims priority to and the benefit as a non-provisional application of U.S. Provisional Patent Application No. 63/432,589, filed on Dec. 14, 2022, the entire contents of which are hereby incorporated by reference and relied upon.

TECHNICAL FIELD

The present disclosure relates generally to medical fluid treatments, and in particular to dialysis fluid treatments that require fluid heating.

BACKGROUND

Due to various causes, a person's renal system can fail. Renal failure produces several physiological derangements. It is no longer possible to balance water and minerals or to excrete daily metabolic load. Toxic end products of metabolism, such as, urea, creatinine, uric acid, and others, may accumulate in a patient's blood and tissue.

Reduced kidney function and, above all, kidney failure is treated with dialysis. Dialysis removes waste, toxins, and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins, and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins, and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. Automated PD machines, however, perform the cycles automatically, typically while the patient sleeps. The PD machines free patients from having to manually perform the treatment cycles and from having to transport supplies during the day. The PD machines connect fluidly to an implanted catheter, to a source or bag of fresh dialysis fluid and to a fluid drain. The PD machines pump fresh dialysis fluid from a dialysis fluid source, through the catheter and into the patient's peritoneal chamber. The PD machines also allow for the dialysis fluid to dwell within the chamber and for the transfer of waste, toxins, and excess water to take place. The source may include multiple liters of dialysis fluid including several solution bags.

The PD machines pump used or spent dialysate from the patient's peritoneal cavity, though the catheter, to drain. As with the manual process, several drain, fill, and dwell cycles occur during dialysis. A "last fill" may occur at the end of an APD treatment. The last fill fluid may remain in the peritoneal chamber of the patient until the start of the next treatment, or may be manually emptied at some point during the day.

In any of the above modalities using an automated machine, component expense, calibration, and maintenance are key design considerations. If a component can be eliminated, not only is its cost eliminated, but potential calibration of the component is eliminated along with its maintenance and/or replacement. Component removal reduces machine weight and also frees space within the machine housing or allows the housing to be made smaller.

For each of the above reasons, it is desirable to provide an APD machine that reduces component expense, calibration, and/or maintenance.

SUMMARY

The present disclosure sets forth an automated peritoneal dialysis ("PD") system, which provides one or more PD treatment improvement. The system includes a PD machine or cycler. The PD machine is capable of delivering fresh, heated PD fluid to a patient at, for example, 14 kPa (2.0 psig) or higher. The PD machine is capable of removing used PD fluid or effluent from the patient at, for example, between −5 kPa (−0.73 psig) and −15 kPa (−2.2 psig), such as −9 kPa (−1.3 psig) or higher. Fresh PD fluid may be delivered via a dual lumen patient line to the patient and is first heated to a body fluid temperature, e.g., 37° C. The heated PD fluid is then pumped through a fresh PD fluid lumen of the dual lumen patient line into a disposable filter set, which is connected to the patient's transfer set, which is in turn connected to an indwelling catheter leading into the patient's peritoneal cavity. The disposable filter set communicates fluidly with the fresh and used PD fluid lumens of the dual lumen patient line. The disposable filter set is provided in one embodiment as a last chance filter for the PD machine, which may be heat disinfected between treatments.

The system may include one or more PD fluid container or bag that supplies fresh PD fluid to the PD machine or cycler. The PD machine or cycler may include internal lines having two-way or three-way valves and at least one PD fluid pump for pumping fresh PD fluid from the one or more PD fluid container or bag to a patient and for removing used PD fluid from the patient to a house drain or drain container. One or more flexible PD fluid line leads from the PD machine or cycler's internal lines to the one or more PD fluid container or bag. The flexible dual lumen patient line mentioned above leads from the PD machine or cycler's internal lines to the patient. A flexible drain line leads from the PD machine or cycler's internal lines to the house drain or drain container. The system, in one embodiment, disinfects all internal lines, the PD fluid lines, and the dual lumen patient line after treatment for reuse in a next treatment. The disinfection may involve heat disinfection using leftover fresh PD fluid.

The PD machine or cycler also includes different types of sensors that output to a control unit of the machine. The different types of sensors include, for example, temperature sensors, pressure sensors, a leak detection sensor, and possibly a flow sensor. The pressure sensors detect PD fluid pressures and are used to control the PD fluid pressures (negative and positive) caused by a PD fluid pump. When the filter set and dual lumen patient line are provided, a filter membrane of the filter set causes a pressure drop in fresh PD fluid pressure. The pressure outputted by the pump to the filter membrane is accordingly greater than the pressure experienced by the patient downstream from the filter membrane due to the pressure drop. The PD fluid pressure downstream from the filter membrane is accordingly an important pressure to monitor for use as feedback to control the PD fluid pump, such that the PD fluid pressure experienced by the patient is at or below a patient PD fluid pressure limit.

One or more pressure sensor is located so as to sense the PD fluid pressure in the used PD fluid lumen of the dual lumen patient line, which is the important pressure downstream of the filter membrane. The pressure sensor positioned to sense the PD fluid pressure in the fresh PD fluid lumen is therefore not as critical and instead is used to sense, for example, kinks or obstructions is the fresh PD fluid lumen. It is accordingly contemplated to eliminate the pressure sensor positioned to sense the PD fluid pressure in the fresh PD fluid lumen and to estimate the PD fluid pressure using an output provided by a driver of a motor that is used to drive the PD fluid pump.

The PD fluid pump is, in one embodiment, a piston pump that includes a housing holding a cylinder within which a piston is actuated via a motor, under control of a motor driver (considered a part of the overall control unit), where the motor drives a motion coupler that is coupled to a piston. The motion coupler converts a rotational motion of the motor to a rotational and translational movement of the piston. The motion coupler moves the piston in and out relative to the cylinder to create positive and negative pumping pressure, respectively. The motion coupler also rotates the piston within the cylinder to move PD fluid from an inlet port to an outlet port.

The motor is, in one embodiment, a stepper motor and the motor driver for the stepper motor provides an output, which is indicative of a load currently seen or experienced by the motor. To estimate the motor load, the motor driver measures electrical energy flowing into the motor and electrical energy flowing out of the motor. The difference between the energy flowing in versus the energy flowing out provides an indication of the mechanical load seen or experienced by the motor. The motor driver measures the portion of the energy fed to the motor that is returned back to a power supply powering the stepper motor. Such spare energy is measurable and is indicative of the mechanical load applied to the motor.

From a point of view of the motor, the load estimation output from the motor driver represents a load angle of the stepper motor, which is dependent on an external torque applied to a motor shaft axis. The stepper motor includes a stator, which is static, and a rotor, which rotates within the stator. A magnetic field is applied when powering the motor, where the magnetic field rotationally pulls and pushes the rotor within the stator, causing a phase shift between a magnetic field direction of the rotor and a magnetic field direction of the rotating field of the stator. The phase shift is the load angle, namely, the angle between the magnetic field direction of the rotor and the magnetic field direction of the rotating magnetic field of the stator. From a mathematical point of view, the load estimation output from the motor driver may be a function of a back electro-motive force ("EMF") constant inherent to the stepper motor, a coil inductance of the stepper motor, a coil resistance of the stepper motor, a step speed (e.g., full step per second), a load angle, a phase current applied to the motor, and a voltage supplied to the stepper motor.

The control unit of the PD system of the present disclosure includes software that converts the load estimation output from the motor driver into an accurate pressure value for the positive PD fluid pressure that is outputted by the PD fluid pump. The conversion software is developed using a machine learning algorithm or model, such as a Gaussian process regression model or a decision tree model. The machine learning algorithm or model is configured to correlate known PD fluid pressures within a patient line with data associated with the load estimation output from the motor driver. The data may be obtained from a sampling of the load estimation output at discrete intervals. For example, thirty to fifty data points may be sampled together and processed to obtain characteristics of the load estimation output from the motor driver, which are used as inputs to the machine learning model, in some embodiments.

The machine learning algorithm includes discrete inputs of characteristics of the load estimation output from the motor driver. The characteristics may include a minimum value of the sampled data, a maximum value of the sampled data, an average value of the sampled data, a median value of the sampled data, and/or a difference of the maximum value and the minimum value (e.g., a range) of the sampled data. In addition to the load estimation, the machine learning algorithm may take into account a flow rate of the PD fluid and/or an upstream pressure. As discussed in more detail below, the disclosed machine learning algorithm provides an accurate estimation of PD fluid pressure within a patient line, thereby enabling a pressure sensor to be removed.

Aspects of the subject matter described herein may be useful alone or in combination with one or more other aspect described herein. Without limiting the foregoing description, in a first aspect of the present disclosure, which may be combined with any other aspect, or portion thereof, a peritoneal dialysis ("PD") system includes a housing, a PD fluid pump housed by the housing, the PD fluid pump including an actuator, e.g., piston, that is actuated by a motor, a patient line fluidly coupling the PD fluid pump to a transfer set that is connected to an indwelling catheter leading into a peritoneal cavity of a patient, a motor driver configured to control the motor and transmit an output signal that is indicative of a load on the motor, and a memory storing a machine learning algorithm that associates data related to output signals from motor drivers with known PD fluid pressures within patient lines. The PD system also includes a processor electrically coupled to the motor driver and the memory. The processor is configured to transmit an input signal to activate the motor driver, receive the output signal from the motor driver, estimate a PD fluid pressure within the patient line by applying the data from the received output signal to the machine learning algorithm, and cause the motor driver to stop when the estimated PD fluid pressure is above a threshold value.

In accordance with a second aspect of the present disclosure, which may be combined with any other aspect, or portion thereof, the processor is further configured to receive a plurality of output signals from the motor driver, sample the plurality of output signals at a specified rate using a moving window filter, and apply the machine learning algorithm to data from the sampled plurality of output signals that are within the moving window filter.

In accordance with a third aspect of the present disclosure, which may be combined with any other aspect, or portion thereof, the specified rate is between 50 Hz and 1000 Hz for sampling between 1 and 100 output signals (preferably about 5 to 7 output signals) within the moving window filter.

In accordance with a fourth aspect of the present disclosure, which may be combined with any other aspect, or portion thereof, the processor is further configured to determine at least one of the following input variable values as the data from the sampled plurality of output signals: (i) a minimum output signal value, (ii) a maximum output signal value, (iii) an average output signal value, (iv) a median output signal value, or (v) a difference of the maximum output signal value and the minimum output signal value, and use the at least one of the (i) to (v) for applying the machine learning algorithm to the sampled plurality of output signals that are within the moving window filter.

In accordance with a fifth aspect of the present disclosure, which may be combined with any other aspect, or portion thereof, the processor is further configured to determine or receive an indication of a flow rate of the PD fluid, and use the flow rate of the PD fluid in conjunction with the at least one of the (i) to (v) for applying the machine learning algorithm to the sampled plurality of output signals that are within the moving window filter.

In accordance with a sixth aspect of the present disclosure, which may be combined with any other aspect, or portion thereof, the processor is further configured to normalize flow rate of the PD fluid by dividing the flow rate of the PD fluid by a maximum flow rate, and use the normalized flow rate of the PD fluid in conjunction with the at least one of the (i) to (v) for applying the machine learning algorithm to the sampled plurality of output signals that are within the moving window filter.

In accordance with a seventh aspect of the present disclosure, which may be combined with any other aspect, or portion thereof, the processor is configured to receive the flow rate of the PD fluid from a flow rate sensor that is fluidly coupled to the patient line or determine the flow rate of the PD fluid from a programmed PD fluid flow rate.

In accordance with an eighth aspect of the present disclosure, which may be combined with any other aspect, or portion thereof, the machine learning algorithm includes the following input variables as inputs: at least one of the flow rate of the PD fluid or a normalized fluid flow rate of the PD fluid, and at least one of (i) a minimum output signal value, (ii) a maximum output signal value, (iii) an average output signal value, (iv) a median output signal value, or (v) a difference of the maximum output signal value and the minimum output signal value.

In accordance with a ninth aspect of the present disclosure, which may be combined with any other aspect, or portion thereof, the machine learning algorithm additionally includes an upstream PD fluid pressure as an input variable.

In accordance with a tenth aspect of the present disclosure, which may be combined with any other aspect, or portion thereof, the machine learning algorithm is trained using a data set that associates at least one of the flow rate of the PD fluid or the normalized fluid flow rate of the PD fluid and the at least one of (i) to (v) with a PD fluid pressure within the patient line that is measured by a pressure sensor.

In accordance with an eleventh aspect of the present disclosure, which may be combined with any other aspect, or portion thereof, the processor is further configured to receive an indication of an upstream PD fluid pressure from a pressure sensor that is located upstream from the PD fluid pump, and use the upstream PD fluid pressure in conjunction with the at least one of the (i) to (v) for applying the machine learning algorithm to the sampled plurality of output signals that are within the moving window filter.

In accordance with a twelfth aspect of the present disclosure, which may be combined with any other aspect, or portion thereof, the upstream PD fluid pressure corresponds to a head height pressure.

In accordance with a thirteenth aspect of the present disclosure, which may be combined with any other aspect, or portion thereof, the PD system further includes a filter set including a hydrophilic filter membrane fluidly coupled between the patient line and the transfer set. In this aspect, the patient line is a dual lumen patient line including a fresh PD fluid lumen and a used PD fluid lumen, and the processor is configured to estimate the fluid pressure within the fresh PD fluid lumen.

In accordance with a fourteenth aspect of the present disclosure, which may be combined with any other aspect, or portion thereof, the motor is a stepper motor and the output signal represents a load angle of the stepper motor.

In accordance with a fifteenth aspect of the present disclosure, which may be combined with any other aspect, or portion thereof, the processor is further configured to apply a smoothing function to a sequence or stream of the estimated PD fluid pressures.

In accordance with a sixteenth aspect of the present disclosure, which may be combined with any other aspect, or portion thereof, a peritoneal dialysis ("PD") method to estimate PD fluid pressure includes storing in a memory of a PD machine, a machine learning algorithm that associates data related to output signals from motor drivers with known PD fluid pressures within patient lines. The method also includes transmitting from a processor of the PD machine to a motor driver of a PD fluid pump, an input signal to activate the motor driver, which causes a motor to actuate an actuator, e.g., piston, for pumping PD fluid at a specified rate from the PD fluid pump to a patient line that is fluidly coupled to a transfer set that is connected to an indwelling catheter leading into a patient's peritoneal cavity. The method further includes receiving, in the processor, output signals from the motor driver that are indicative of a load estimation output of the motor, estimating, via the processor using the machine learning algorithm, a PD fluid pressure within the patient line based on the data related to the received output signals, and causing, via the processor, a user interface of the PD machine to display the estimated PD fluid pressure.

In accordance with a seventeenth aspect of the present disclosure, which may be combined with any other aspect, or portion thereof, the method further includes causing, via the processor, the motor driver to stop when the estimated PD fluid pressure is above a threshold value out outside of a specified range.

In accordance with an eighteenth aspect of the present disclosure, which may be combined with any other aspect, or portion thereof, the machine learning algorithm includes at least one of a Gaussian process regression, a linear regression, a logic regression, a decision tree, a gradient boosting algorithm, a random forest algorithm, a k-nearest neighbor algorithm, a k-means algorithm, a support-vector machine, a Naïve Bayes algorithm or combinations thereof.

In accordance with a nineteenth aspect of the present disclosure, which may be combined with any other aspect, or portion thereof, the method further includes sampling, via the processor, the output signals at a specified rate using a moving window filter, and applying, via the processor, the machine learning algorithm to data from the sampled plurality of output signals that are within the moving window filter.

In accordance with a twentieth aspect of the present disclosure, which may be combined with any other aspect, or portion thereof, the specified rate is between 50 Hz and 1000 Hz for sampling between 1 and 100 output signals (preferably between 5 to 7 output signals) within the moving window filter.

In accordance with a twenty-first aspect of the present disclosure, which may be combined with any other aspect, or portion thereof, the method further includes determining, via the processor, at least one of the following input variable values as the data from the sampled output signals: (i) a minimum output signal value, (ii) a maximum output signal value, (iii) an average output signal value, (iv) a median output signal value, or (v) a difference of the maximum output signal value and the minimum output signal value, and using, via the processor, the at least one of the (i) to (v)

for applying the machine learning algorithm to the sampled plurality of output signals that are within the moving window filter.

In accordance with a twenty-second aspect of the present disclosure, which may be combined with any other aspect, or portion thereof, the method further includes determining or receiving, via the processor, an indication of a flow rate of the PD fluid, and using, via the processor, the flow rate of the PD fluid in conjunction with the at least one of the (i) to (v) for applying the machine learning algorithm to the sampled plurality of output signals that are within the moving window filter.

In accordance with a twenty-third aspect of the present disclosure, which may be combined with any other aspect, or portion thereof, the method further includes training the machine learning algorithm using a data set that associates at least one of the flow rate of the PD fluid or the normalized fluid flow rate of the PD fluid and the at least one of (i) to (v) with a PD fluid pressure within the patient line that is measured by a pressure sensor.

In a twenty-fourth aspect of the present disclosure, which may be combined with any other aspect, or portion thereof, any of the features, functionality and alternatives described in connection with any one or more of FIGS. 1 to 10 may be combined with any of the features, functionality and alternatives described in connection with any other of FIGS. 1 to 10.

In light of the above aspects and present disclosure set forth herein, it is an advantage of the present disclosure to provide a PD system and associated methodology that estimates PD fluid pressure using a motor driver output.

It is another advantage of the present disclosure to provide a PD system and associated methodology that eliminates a pressure sensor for measuring a pressure of PD fluid in a patient line.

It is a further advantage of the present disclosure to provide a PD system and associated methodology that uses a machine learning to estimate the PD fluid pressure using a load on a PD fluid pump.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the improvements or advantages listed herein, and it is expressly contemplated to claim individual advantageous embodiments separately. In particular, the system of the present disclosure may have any one or more or all of the drip prevention structure and methodology, PD fluid container emptying structure and methodology and patient connection before drain check structure and methodology described herein. Moreover, it should be noted that the language used in the specification has been selected principally for readability and instructional purposes, and not to limit the scope of the inventive subject matter.

BRIEF DESCRIPTION OF THE DRAWINGS

FIG. 5 shows a flow diagram illustrating an example procedure to estimate a pressure of PD fluid within the patient line of the PD system of FIGS. 1 to 3 using the machine learning algorithm of FIG. 4, according to an example embodiment of the present disclosure.

DETAILED DESCRIPTION

A PD system is disclosed herein that estimates a PD fluid pressure within a patient line downstream from a PD fluid pump. The example PD system is configured to use a load estimation output from a motor driver of the PD fluid pump to estimate the PD fluid pressure. To perform the pressure estimation, the PD system uses a machine learning algorithm, such as a Gaussian process regression model or a decision tree model. The machine learning algorithm or model is configured to correlate known PD fluid pressures within a patient line with data associated with the load estimation output from the motor driver. The data may be obtained from a sampling of the load estimation output at discrete intervals. For example, thirty to fifty data points may be sampled together and processed to obtain characteristics of the load estimation output from the motor driver, which are used as inputs to the machine learning model, in some embodiments.

The machine learning algorithm includes discrete inputs of characteristics of the load estimation output from the motor driver. The characteristics may include a minimum value of the sampled data, a maximum value of the sampled data, an average value of the sampled data, a median value of the sampled data, and/or a difference of the maximum value and the minimum value (e.g., a range) of the sampled data. In addition to the load estimation, the machine learning algorithm may take into account a flow rate of the PD fluid and/or an upstream pressure. As discussed in more detail below, the disclosed machine learning algorithm provides an accurate estimation of PD fluid pressure within a patient line, thereby enabling a pressure sensor to be removed.

Reference is made herein to PD systems that include a cycler. It should be appreciated that the systems and methods disclosed herein may applied to any pressure estimation that is downstream from a pump. For example, the methods and systems may be used for hemodialysis, hemofiltration, hemodiafiltration, and continuous renal replacement machines for downstream pressure from a blood pump or a dialysis fluid pump. The systems and methods may also be used for infusion pumps or syringe pumps. Further, the systems and methods may be used for parenteral nutrition pumps or patient-controlled analgesia pumps.

Further, while reference is made herein to the PD fluid pressure estimation being used to remove the need for a downstream pressure sensor, it should be appreciated that the PD fluid pressure estimation may also be used for cycler diagnostics. For example, the estimated pressure may be compared to a measured pressure to determine when a non-dynamic load of a pump begins to deviate. When the deviation is significant, the system and methods disclosed hereby may indicate that a PD fluid pump needs servicing or replacement.

System Overview

Figure 1:
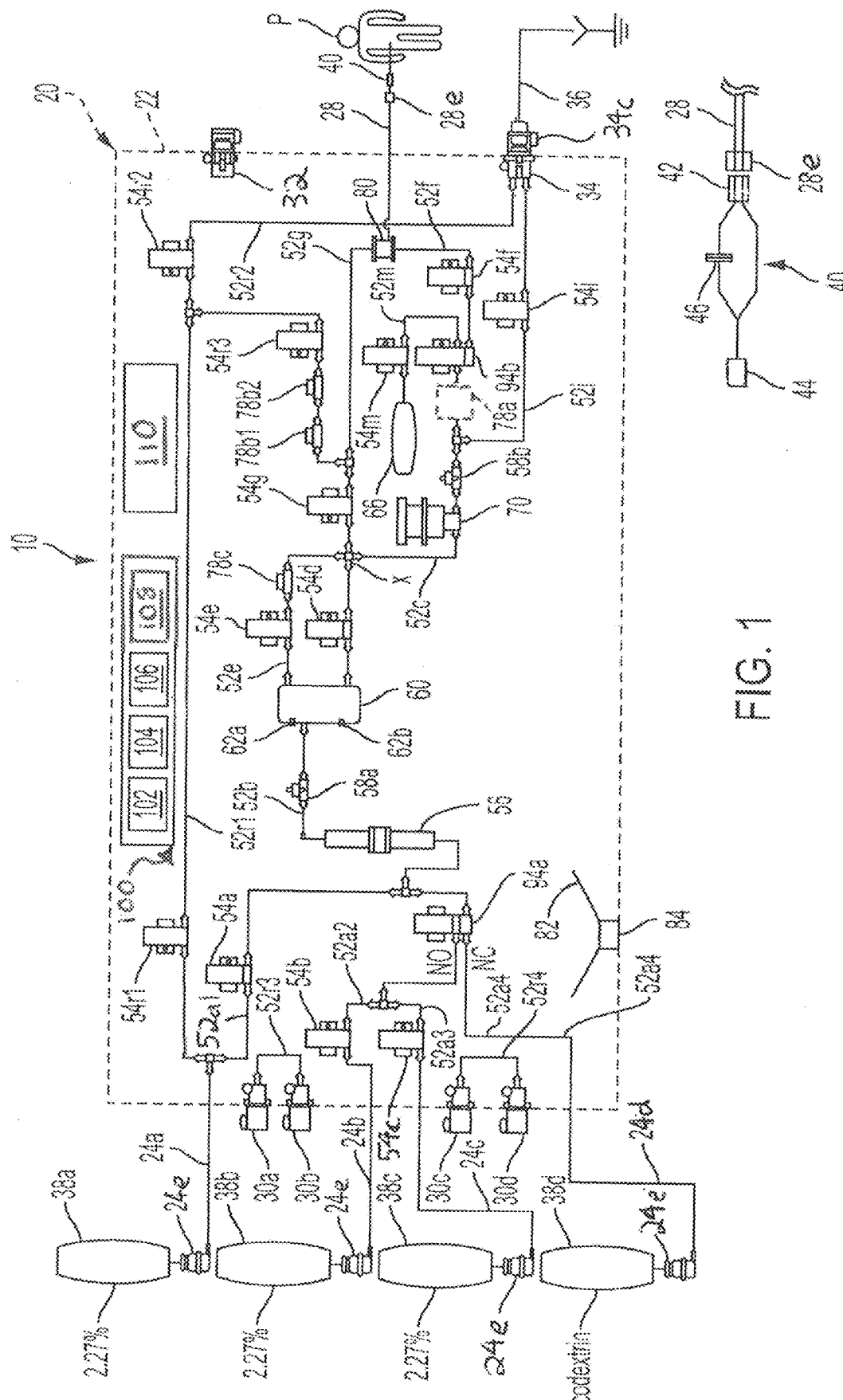
FIG. 1 is a fluid flow schematic of one embodiment for a PD system in a treatment state, according to an example embodiment of the present disclosure.

Referring now to the drawings and in particular to FIG. 1, a medical system having the motor driver pressure estimation of the present disclosure is illustrated via peritoneal dialysis ("PD") system 10. System 10 includes a PD machine or cycler 20 and a control unit 100 including one or more processor 102, one or more memory 104, video controller 106, a motor driver 108, and user interface 110. User interface 110 may alternatively or additionally be a remote user interface, e.g., via a tablet or smartphone. Control unit 100 may also include a transceiver and a wired or wireless connection to a network (not illustrated), e.g., the internet, for sending treatment data to and receiving prescription instructions/changes from a doctor's or clinician's server interfacing with a doctor's or clinician's computer. Control unit 100, in an embodiment, controls all electrical fluid flow and heating components of system 10 and receives outputs from all sensors of system 10. System 10 in the illustrated embodiment includes durable and reusable components that contact fresh and used PD fluid, for example, which necessitates that PD machine or cycler 20 be disinfected between treatments, e.g., via heat disinfection.

System 10 in FIG. 1 includes an inline resistive heater 56, reusable supply lines or tubes 52*al* to 52*a4* and 52*b*, air trap 60 operating with respective upper and lower level sensors 62*a* and 62*b*, air trap valve 54*d*, vent valve 54*e* located along vent line 52*e*, reusable line or tubing 52*c*, PD fluid pump 70, temperature sensors 58*a* and 58*b*, pressure sensors (78*a* shown in dashed line as removed and replaced with motor driver estimation), 78*b1*, 78*b2* and 78*c*, reusable patient tubing or lines 52*f* and 52*g* having respective valves 54*f* and 54*g*, dual lumen patient line 28, a hose reel 80 for retracting patient line 28, reusable drain tubing or line 52*i* extending to drain line connector 34 and having a drain line valve 54*i*, and reusable recirculation disinfection tubing or lines 52*r1* and 52*r2* operating with respective disinfection valves 54*r1* and 54*r2*. A third recirculation or disinfection tubing or line 52*r3* extends between disinfection or PD fluid line connectors 30*a* and 30*b* for use during disinfection. A fourth recirculation or disinfection tubing or line 52*r4* extends between disinfection connectors 30*c* and 30*d* for use during disinfection.

System 10 also includes PD fluid containers or bags 38*a* to 38*c* (e.g., holding the same or different formulations of PD fluid), which connect to distal ends 24*e* of reusable PD fluid lines 24*a* to 24*c*, respectively. System 10 further includes a fourth PD fluid container or bag 38*d* that connects to a distal end 24*e* of reusable PD fluid line 24*d*. Fourth PD fluid container or bag 38*d* may hold the same or different type (e.g., icodextrin) of PD fluid than provided in PD fluid containers or bags 38a to 38c. Reusable PD fluid lines 24a to 24d extend in one embodiment through apertures (not illustrated) defined or provided by housing 22 of PD machine 20.

System 10 in the illustrated embodiment includes four disinfection or PD fluid line connectors 30a to 30d for connecting to distal ends 24e of reusable PD fluid lines 24a to 24d, respectively, during disinfection. System 10 also provides a patient line connector 32 that includes an internal lumen, e.g., a U-shaped lumen, which for disinfection directs fresh or used dialysis fluid from one PD fluid lumen of a connected distal end 28e of dual lumen patient line 28 into the other PD fluid lumen. Reusable supply tubing or lines 52a1 to 52a4 communicate with reusable supply lines 24a to 24d, respectively. Reusable supply tubing or lines 52a1 to 52a3 operate with valves 54a to 54c, respectively, to allow PD fluid from a desired PD fluid container or bag 38a to 38c to be pulled into PD machine 20. Three-way valve 94a in the illustrated example allows for control unit 100 to select between (i) 2.27% (or other) glucose dialysis fluid from container or bag 38b or 38c and (ii) icodextrin from container or bag 38d. In the illustrated embodiment, icodextrin from container or bag 38d is connected to the normally closed port of three-way valve 94a.

System 10 is constructed in one embodiment such that drain line 52i during a patient fill is fluidly connected downstream from PD fluid pump 70. In this manner, if drain valve 54i fails or somehow leaks during the patient fill of patient P, fresh PD fluid is pushed down disposable drain line 36 instead of used PD fluid potentially being pulled into pump 70. Disposable drain line 36 is in one embodiment removed for disinfection, wherein drain line connector 34 is capped via a cap 34c to form a closed disinfection loop. PD fluid pump 70 may be an inherently accurate pump, such as a piston pump, or less accurate pump, such as a gear pump that operates in cooperation with a flowmeter (not illustrated) to control fresh and used PD fluid flowrate and volume.

System 10 may further include a leak detection pan 82 located at the bottom of housing 22 of PD machine 20 and a corresponding leak detection sensor 84 outputting to control unit 100. In the illustrated example, system 10 is provided with an additional pressure sensor 78c located upstream of PD fluid pump 70, which allows for the measurement of the suction pressure of pump 70 to help control unit 100 more accurately determine pump volume. Additional pressure sensor 78c in the illustrated embodiment is located along vent line 52e, which may be filled with air or a mixture of air and PD fluid, but which should nevertheless be at the same negative pressure as PD fluid located within PD fluid line 52c.

System 10 in the example of FIG. 1 includes redundant pressure sensors 78b1 and 78b2, the output of one of which is used for pump control, as discussed herein, while the output of the other pressure sensor is a safety or watchdog output to make sure the control pressure sensor is reading accurately. Pressure sensors 78b1 and 78b2 are located along a line including a third recirculation valve 54r3. System 10 may further employ one or more cross, marked via an X in FIG. 1, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve 94b via a citric acid valve 54m located along a citric acid line 52m. Citric acid line 52m is connected in one embodiment to the normally closed port of second three-way valve 94b, so as to provide redundant valves between citric acid container or bag 66 and the PD fluid circuit during treatment. The redundant valves ensure that no citric (or other) acid reaches the treatment fluid lines during treatment. Citric (or other) acid is used instead during disinfection.

Control unit 100 in an embodiment uses feedback from any one or more of pressure sensors 78b1 or 78b2 to enable PD machine 20 to deliver fresh, heated PD fluid to the patient at, for example, 14 kPa (2.0 psig) or higher. The pressure feedback is used to enable PD machine 20 to remove used PD fluid or effluent from the patient at, for example, between −5 kPa (−0.73 psig) and −15 kPa (−2.2 psig), such as −9 kPa (−1.3 psig) or higher (more negative). The pressure feedback may be used in a proportional, integral, derivative ("PID") pressure routine for pumping fresh and used PD fluid at a desired positive or negative pressure.

Inline resistive heater 56 under control of control unit 100 is capable of heating fresh PD fluid to body temperature, e.g., 37° C., for delivery to patient P at a desired flowrate. Control unit 100 in an embodiment uses feedback from temperature sensor 58a in a PID temperature routine for pumping fresh PD fluid to patient P at a desired temperature.

FIG. 1 also illustrates that system 10 includes and uses a disposable filter set 40, which communicates fluidly with the fresh and used PD fluid lumens of dual lumen patient line 28. Disposable filter set 40 includes a disposable connector 42 that connects to a distal end 28e of reusable patient line 28. Disposable filter set 40 also includes a connector 44 that connects to the patient's transfer set. Disposable filter set 40 further includes a sterilizing grade hydrophilic filter membrane 46 that further filters fresh PD fluid. Disposable filter set 40 is provided in one embodiment as a last chance filter for PD machine 20, which has been heat disinfected between treatments. Any pathogens that may remain after disinfection, albeit unlikely, are filtered from the PD fluid via the hydrophilic membrane 46 of disposable filter set 40.

FIG. 1 illustrates system 10 setup for treatment with PD fluid containers or bags 38a to 38d connected via reusable, flexible PD fluid lines 24a to 24d, respectively. Dual lumen patient line 28 is connected to patient P via disposable filter set 40. Disposable drain line 36 is connected to drain line connector 34. In FIG. 1, PD machine or cycler 20 of system 10 is configured to perform multiple patient drains, patient fills, patient dwells, and a priming procedure, as part of or in preparation for treatment.

Figure 2:
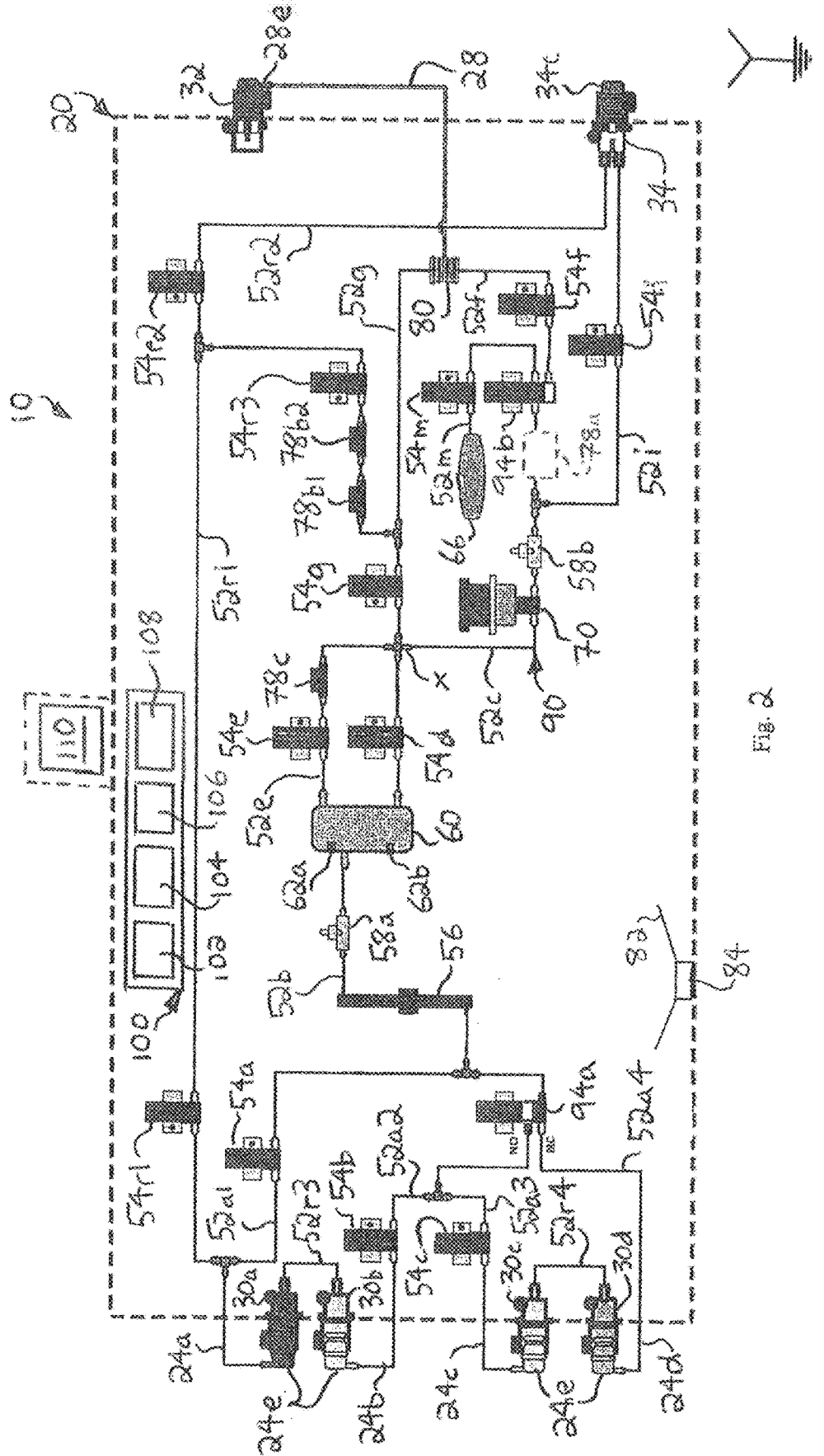
FIG. 2 is a fluid flow schematic of one embodiment for a PD system in a disinfection state, according to an example embodiment of the present disclosure.

FIG. 2 illustrates system 10 in a disinfection mode. PD fluid containers or bags 38a to 38d are removed and flexible PD fluid lines 24a to 24d are plugged instead in a sealed manner into disinfection or PD fluid line connectors 30a to 30d, respectively. Reusable Dual lumen patient line 28 is disconnected from disposable filter set 40 (which is discarded), and distal end 28e of dual lumen patient line 28 is plugged sealingly into patient line connector 32. Disposable drain line 36 is removed from drain line connector 34 and discarded. Drain line connector 34 is capped via cap 34c to form a closed disinfection loop 90. PD machine or cycler 20 of system 10 in FIG. 2 is configured to perform a disinfection sequence, e.g., a heat disinfection sequence, in which fresh PD fluid is heated via inline heater 56 to a disinfection temperature, e.g., 70° C. to 90° C. PD fluid pump 70 circulates the heated PD fluid closed disinfection loop 90 for an amount of time needed to properly disinfect the fluid components and lines of the disinfection loop.

Motor Driver Pressure Estimation Embodiment

Hydrophilic filter membrane 46 of filter set 40 causes a pressure drop in fresh PD fluid pressure. The pressure outputted by PD fluid pump 70 through the fresh PD fluid lumen of dual lumen patient line 28 to hydrophilic filter membrane 46 is accordingly greater than the pressure experienced by patient P downstream from hydrophilic filter membrane 46 due to the pressure drop. The PD fluid pressure downstream from hydrophilic filter membrane 46 is accordingly the important pressure to monitor for use as feedback to control the PD fluid pump 70, such that the PD fluid pressure experienced by patient P is at or below the patient PD fluid pressure limits listed above.

Pressure sensors 78*bl*, 78*b2* are located so as to sense the PD fluid pressure in the used PD fluid lumen of dual lumen patient line 28, which is the important pressure downstream of the filter membrane. A pressure sensor 78*a* positioned to sense the PD fluid pressure in the fresh PD fluid lumen is therefore not as critical and instead is used to sense, for example, kinks or obstructions is the fresh PD fluid lumen. It is accordingly contemplated to eliminate pressure sensor 78*a* (shown in dashed line) positioned to sense the PD fluid pressure in the fresh PD fluid lumen and to instead estimate the PD fluid pressure using an output signal provided by motor driver 108 for the motor (e.g., stepper motor) used to drive PD fluid pump 70.

PD fluid pump 70 is, in one embodiment, a piston pump that includes a housing holding a cylinder within which a piston is actuated via a motor, under control of motor driver 108 (considered a part of overall control unit 100), where the motor drives a motion coupler coupled to a piston. The motion coupler converts a rotational motion of the motor to a rotational and translational movement of the piston. The motion coupler moves the piston in and out relative to the cylinder to create positive and negative pumping pressure, respectively. The motion coupler also rotates the piston within the cylinder to move PD fluid from an inlet port to an outlet port of the PD fluid pump 70.

The motor is, in one embodiment, a stepper motor and the motor driver 108 for the stepper motor provides an output signal, which is indicative of a load currently seen or experienced by the motor. To estimate the motor load, motor driver 108 in one embodiment measures electrical energy flowing into the motor and electrical energy that flows out of the motor. The difference between the energy flowing in versus the energy flowing out provides an indication of the mechanical load seen or experienced by the motor. Motor driver 108 measures the portion of the energy fed to the motor that is returned back to a power supply powering the stepper motor. Such spare energy is measurable and is indicative of the mechanical load applied to the motor.

From a point of view of the motor, the load estimation output from motor driver 108 represents a load angle of the stepper motor, which is dependent on an external torque applied to a motor shaft axis. The stepper motor includes a stator, which is static, and a rotor, which rotates within the stator. A magnetic field is applied when powering the motor, where the magnetic field rotationally pulls and pushes the rotor within the stator, causing a phase shift between a magnetic field direction of the rotor and a magnetic field direction of the rotating field of the stator. The phase shift is the load angle, namely, the angle between the magnetic field direction of the rotor and the magnetic field direction of the rotating magnetic field of the stator.

From a mathematical point of view, the load estimation output ("LEO") from motor driver 108 may be a function of a back electro-motive force ("EMF") constant inherent to the stepper motor, a coil inductance of the stepper motor, a coil resistance of the stepper motor, a step speed (e.g., full step per second), a load angle, a phase current applied to the motor, and a voltage supplied to the stepper motor.

The motor driver 108 is configured to receive one or more input signals from the processor 102 for controlling pump strokes of the PD fluid pump 70. The one or more input signals may specify a rate and/or duration the motor driver 108 is to actuate the motor. The input signals may be analog or digital. For analog signals, the motor driver 108 controls the motor based on, for example, an amplitude and/or frequency of the input signals. For digital signals, the motor driver 108 uses a look-up table to convert the digital signal into a rate and/or duration for controlling the motor.

Figure 3:
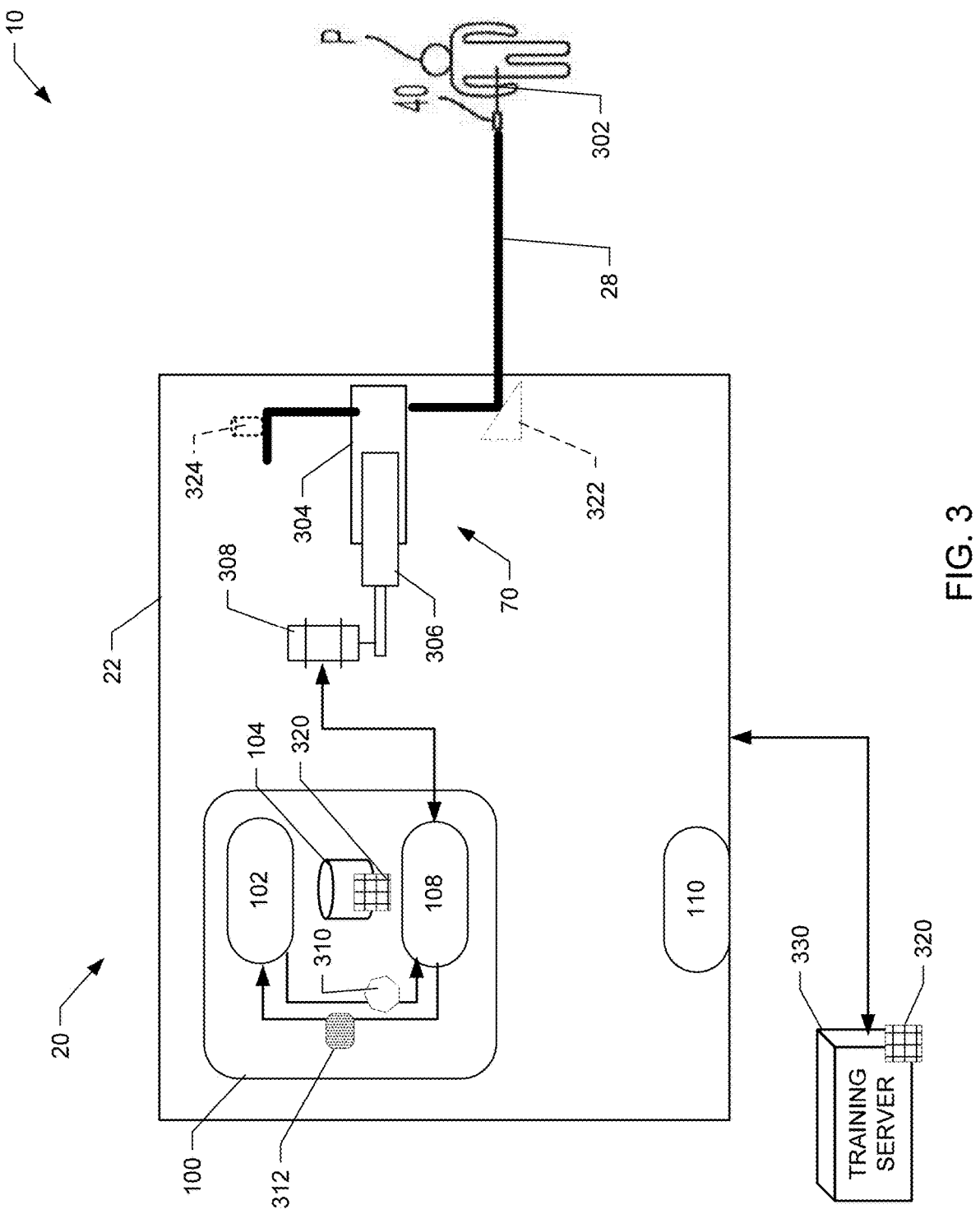
FIG. 3 is a diagram showing features of the PD system that are related to estimating a pressure of PD fluid within a dual lumen patient line, according to an example embodiment of the present disclosure.

FIG. 3 is a diagram showing features of the PD system 10 that are related to estimating a pressure of PD fluid within the dual lumen patient line 28, according to an example embodiment of the present disclosure. As discussed above in connection with FIGS. 1 and 2, the PD system 10 includes PD machine or cycler 20 that is fluidly coupled to the patient P via the dual lumen patient line 28. PD machine 20 includes the control unit 100, which includes at least one processor, the memory 104, and the motor driver 108. Further, the user interface 100 is communicatively coupled to the control unit 100 to enable a user to control the PD machine 20.

FIG. 3 illustrates that the housing 22 of PD machine 20 is configured to enclose or otherwise support the PD fluid pump 70. As discussed above in connection with FIGS. 1 and 2, the PD fluid pump 70 is configured to move PD fluid from the PD machine 20 (e.g., from the PD fluid containers 38) to a peritoneal cavity of a patient P via the dual lumen patient line 28, the disposable filter set 40, and/or a transfer set 302. As discussed above in connection with FIGS. 1 and 2, the transfer set 302 may include or connect to an indwelling catheter leading into the patient's peritoneal cavity. In some embodiments, the disposable filter set 40 may be omitted such that the dual lumen patient line 28 is fluidly coupled directly to the transfer set.

Further, while reference is made to the dual lumen patient line 28, it should be appreciate that the dual lumen patient line 28 may be a single lumen, where the transfer set includes separate connections for receiving fresh PD fluid from PD machine 20 and pulling spent PD fluid to the disposable drain line 36.

FIG. 3 illustrates that PD fluid pump 70 is housed by housing 22 and electrically connected to the motor driver 108. PD fluid pump 70, in one embodiment, is a piston pump that includes a cylinder 304 and a piston 306, which is actuated by a motor 308. The piston 306 is configured to move back and forth within the cylinder 304 to pump fresh PD fluid into the patient line 28. The motor 308 is configured to drive a motion coupler that is connected to the piston 306, which causes the piston 306 to move in and out relative to the cylinder 304 to create positive and negative pumping pressure. The motion coupler converts the rotation motion of the motor 308 to a rotational and translational movement of the piston 308. The motion coupler may also rotate the piston 306 within the cylinder 304 to move the fresh PD fluid from an inlet port to an outlet port of the PD fluid pump 70.

As shown in FIG. 3, the processor 102 is configured to transmit an input signal 310 to the motor driver 108 to cause the PD fluid pump 70 to activate. The input signal 310 may be analog and/or digital and specify a pump rate and/or a duration. In some embodiments, the input signal 310 specifies a pump rate such that the processor 102 continues to transmit the input signal 310 as long as the PD fluid pump 70 is to remain active. In another example, the input signal 310 may specify a number of pump strokes to be pumped. In response to the input signal 310, the motor driver 108 transmits a signal to the motor 308. The signal causes the motor 308 to rotate at the specified speed. The motor driver 108 continues to apply the signal to the motor 308 as long as the motor is to be activated.

The example motor driver 108 is configured to receive feedback indicative of a speed/rotation of the motor 308 in addition to a load angle of the motor 308. The speed/rotation of the motor 308 is used by the motor driver 108 as feedback to speed up or slow down the motor 308 based to meet a specified pumping speed and/or duration. The motor driver 108 is configured to convert the load angle to a load estimation value, which is transmitted in one or more output signals 312 (e.g., a load estimation output ("LEO")) to the processor 102. It should be appreciated that the motor driver 108 provides a near-continuous stream of output signals 312 as long as the motor 308 is active. This stream of output signals 312 enables the processor 102 to determine how the estimated load on the motor 308 changes over time during the pumping of PD fluid. In one embodiment, the PD fluid pump 70 includes a TMC5130 or TMC5160 stepper motor driver produced by Trinamic Motion Control GmbH & Co. KG and the output signals 312 are stallGuard™ signals.

The example memory device 104 of FIG. 3 includes or stores one or more machine learning algorithms 320 that is/are configured to estimate a PD fluid pressure within the patient line 28 based on one or more of the output signals 312 from the motor driver 108. The machine learning algorithm 320 may be specified by one or more instructions that are executable by the processor 102 to perform the operations disclosed herein. As discussed above, the use of the machine learning algorithm 320 enables a pressure sensor on the patient line 28 to be removed or eliminated, thereby saving space and cost.

Figure 4:
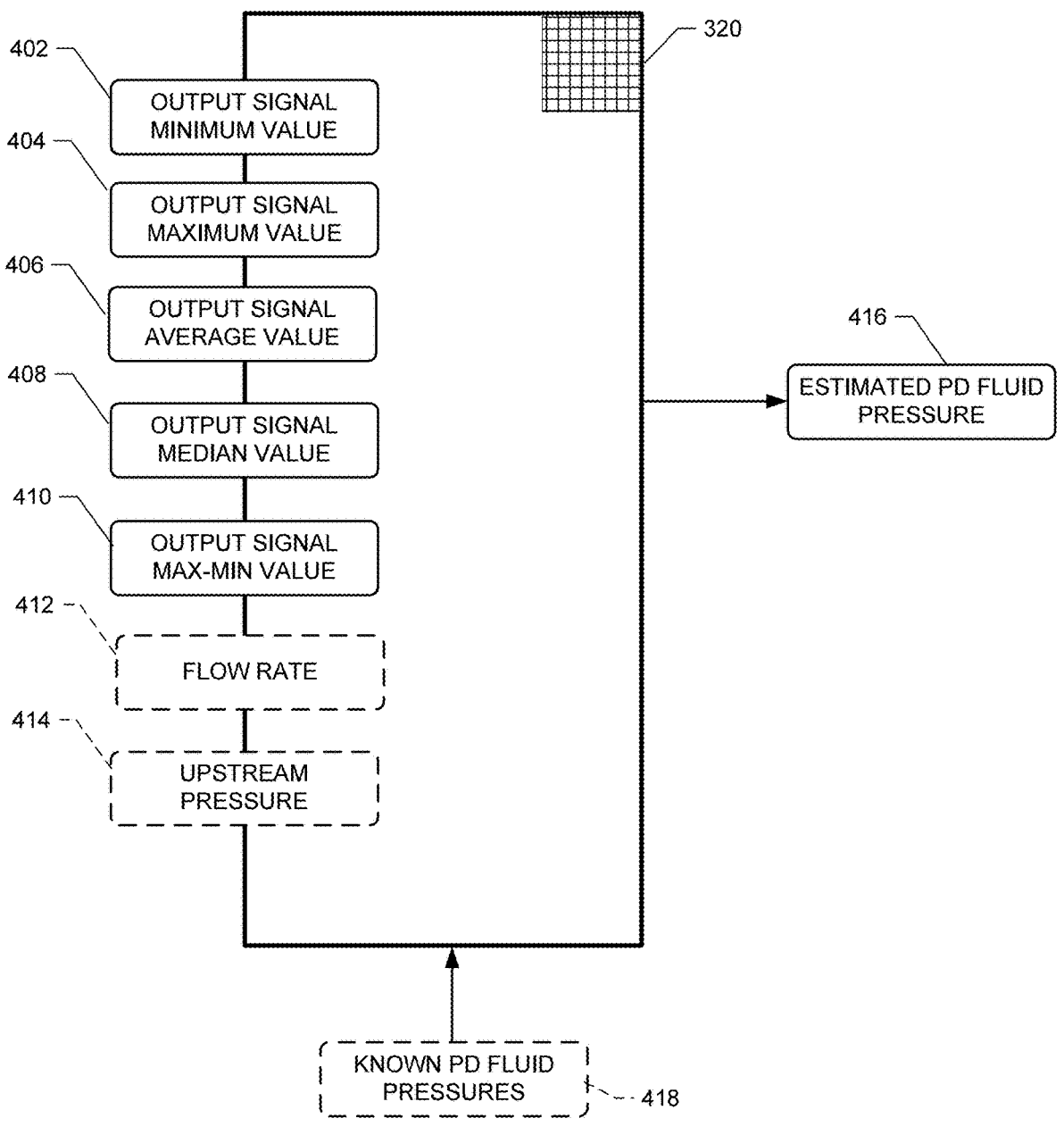
FIG. 4 is a diagram illustrative of a machine learning algorithm of the PD system for estimating pressure in a patient line, according to an example embodiment of the present disclosure.

FIG. 4 is a diagram illustrative of the machine learning algorithm 320 of FIG. 3, according to an example embodiment of the present disclosure. The machine learning algorithm 320 may include a Gaussian process regression, a linear regression, a logic regression, a decision tree, a gradient boosting algorithm, a random forest algorithm, a k-nearest neighbor algorithm, a k-means algorithm, a support-vector machine, a Naïve Bayes algorithm, or combinations thereof. The example machine learning algorithm 320 is configured to receive from the processor 102 a sample of a plurality of the output signals 312. For instance, the processor 102 may be configured to sample the plurality of output signals 312 at a specified rate using a moving window feature. The processor 102 then applies the machine learning algorithm 320 to data corresponding to the sampled plurality of output signals that are within the moving window filter. The specified rate may be between 50 Hz and 1000 Hz for sampling between 1 and 100 output signals 312 within the moving window filter. Preferably, the specified rate is between 100 Hz and 250 Hz for sampling between 5 to 7 output signals.

As shown in FIG. 4, for each sample of the output signals 312, the processor 102 determines certain characteristics of the sampled data including, for example, a minimum value of the output signals 402, a maximum value of the output signals 404, an average value of the output signals 406, a median value of the output signals 408, and a difference of the maximum value and the minimum value (e.g., a range) of the output signals 410. In some embodiments, fewer or additional values 402 to 410 may be used as inputs to the machine learning model 320. For example, the median value 406 may be omitted and/or an average derivative value may be used. In some embodiments, the values 402 to 410 may be normalized.

In some embodiments, the machine learning model 320 may also use a flow rate 412 and/or an upstream pressure value 414. The flow rate 412 may be determined using a flow sensor, such as the flow sensor 322 shown in FIG. 3 on the patient line 28. In these embodiments, the flow sensor 322 transmits data to the processor 102 that is indicative of a measured flow rate 412 of the PD fluid within the patient line 28. Additionally or alternatively, the processor 102 determines the flow rate 412 from a programmed PD fluid flow rate. In this example, the processor 102 may receive program instructions for the PD machine 20 to perform a dialysis treatment. The programed instructions include, for example, a flow rate of PD fluid during fill phases. When the flow rate 412 is not specified, the processor 102 determines the flow rate 412 based on a volume to pump per a time to pump the volume, and/or a specified flow rate for the PD motor driver 108. In some instances, the processor 102 is configured to normalize the flow rate 412 by dividing the flow rate by a maximum flow rate. The normalization may be based on properties of the fluid being pumped, such as water or PD fluid.

In some embodiments, the machine learning model 320 may determine an area under a curve indicative of the sampled set of output signals 312. The machine learning model 320 may be configured to receive an area associated with one revolution of the PD fluid pump 70. The processor 102 may calculate this integral over one revolution to provide a good estimation of the operation of the PD fluid pump 70.

The upstream pressure value 414 corresponds to a pressure measurement provided by a sensor that is upstream of the PD fluid pump 70, such as the pressure sensor 324 shown in FIG. 3. The use of the upstream pressure provides an absolute pressure for the machine learning algorithm 320 rather than determining a relative pressure.

As shown in FIG. 4, the machine learning algorithm 320 is configured to receive one or more of the input values 402 to 414 for the sampled set of output signals 312. The machine learning algorithm 320 uses a Gaussian process regression and/or a decision tree model, for example, to estimate a pressure 416 of PD fluid within the patient line 28 based on the one or more of the input values 402 to 414. In some embodiments, the one or more of the input values 402 to 414 are applied to a single machine learning model 320. In other embodiments, the input values 402 to 410 are applied to a first machine learning model that is then cascaded with a second machine learning model. In this embodiment, the second machine learning model is configured to process an output from the first machine learning model with the flow rate 412 and/or the upstream pressure 414 to generate the estimated pressure 416. In yet other embodiments, the second machine learning model uses the result from the first machine learning model with the flow rate to generate a result, which is then provided as an input to a third machine learning model in addition to the upstream pressure.

Returning to FIG. 3, the processor 102 may display the estimated pressure 416 of the PD fluid within the patient line 28 on a display screen of the user interface 110. Additionally or alternatively, the processor 102 is configured to compare the estimated pressure 416 to a threshold and/or pressure range. Exceeding the threshold may be indicative of an occlusion within the patient line 28, clogging (partial clogging) of the disposable filter set 40 (when used), clogging of the patient catheter, a patient having a full peritoneal cavity, etc. Further, for a range failing to meet a minimum of the range when the PD fluid pump 70 is active may be indicative of a fluid leak. The processor 102 may be configured to cause the user interface 110 to display an alarm or alert when the estimated pressure 416 exceeds the threshold and/or is outside of a specified range. Further, the processor 102 may cause the PD fluid pump 70 to stop operating when the threshold is exceed or the estimated pressure 416 is outside the specified range.

FIG. 5 shows a flow diagram illustrating an example procedure 500 to estimate a pressure of PD fluid within the patient line 28 of the PD machine 20 of FIGS. 1 to 3 using the machine learning algorithm 320 of FIG. 4, according to an example embodiment of the present disclosure. The example procedure 500 may be carried out by, for example, the processor 102, or more generally the control unit 100, described in conjunction with FIGS. 1 to 3. Although the procedure 500 is described with reference to the flow diagram illustrated in FIG. 5, it should be appreciated that many other methods of performing the functions associated with the procedure 500 may be used. For example, the order of many of the blocks may be changed based on a number of machine learning algorithms and inputs used, certain blocks may be combined with other blocks, and many of the blocks described are optional. The operations described in conjunction with the procedure 500 may be specified by one or more instructions that are stored, for example, on the memory 104 of the PD machine 20.

The example procedure begins when the processor 102 receives an instruction 501 to activate the PD fluid pump 70 (block 502). The instruction 501 may include an electronic PD treatment prescription that specifies parameters for performing a PD therapy. The parameters may include a concentration of the PD fluid, a number of PD cycles, a start time, a volume of the fresh PD fluid to be provided for each cycle, a flow rate for the fresh PD fluid, a dwell time, and/or a volume of spent PD fluid to be removed from a patient for each cycle. The processor 102 is configured to use the provided flow rate (and/or pump duration) or determine a flow rate (and/or pump duration) based on the instructions 501. In some embodiments, the instructions 501 may only include a request from a patient or clinician to begin a PD treatment. When the treatment is specified to begin, the processor 102 transmits an input signal 310 to the motor driver 108, causing the motor 308 to actuate (block 504). As discussed above, the input signal 310 may specified a speed and/or duration for actuating the motor 308.

Figure 6:
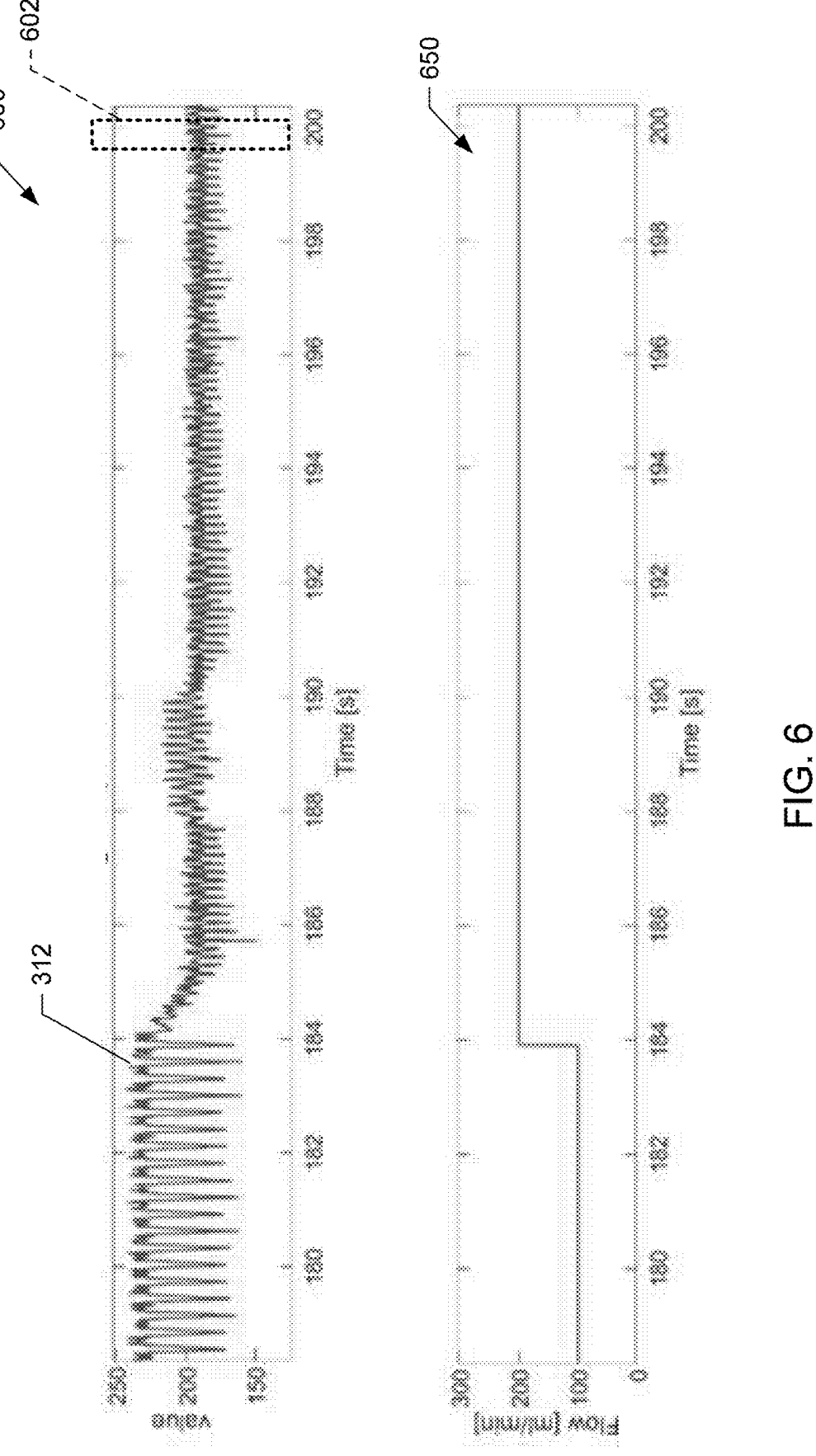
FIG. 6 shows a graph of a stream of output signals and a corresponding flow rate of PD fluid for the PD system of FIGS. 1 to 3, according to an example embodiment of the present disclosure.

The processor 102 then receives a stream of output signals 312 from the motor driver 108 that are indicative of a load on the motor 308 (block 506). Graph 600 of FIG. 6 shows an example of a stream of output signals 312 received by the processor 102 from the motor driver 108, according to an example embodiment of the present disclosure. Each data point within the graph 600 specifies a value that is indicative of a load experienced by the motor 108. The processor 102 combines the data from the output signals 312 into a time-series graph. The processor 102 also applies a moving window filter 602 to sample the data within the graph 600. The window filter 602 may sample the output signals 312 at a specified rate that may be between 50 Hz and 1000 Hz for sampling between 1 and 100 data points, preferably around 5 to 7 data points. The processor 102 is configured to move the window filter 602 as new output signals 312 are received.

Returning to FIG. 5, the processor 102 next determines inputs 402 to 410 from the output signals 312 (block 508). The inputs 402 to 410 are specifically determined from the output signal 312 data that is within the window filter 602. As discussed above, the inputs include the minimum value of the output signals 402 within the window filter 602, the maximum value of the output signals 404 within the window filter 602, the average value of the output signals 406 within the window filter 602, the median value of the output signals 408 within the window filter 602, and the difference of the maximum value and the minimum value (e.g., a range) of the output signals 410 within the window filter 602. In some embodiments, the processor 102 is also configured to receive the flow rate input value 412 from the flow sensor 322 (or determine the flow rate from the instructions 501) and/or the upstream pressure input value 414 from the pressure sensor 324 (block 510). In some instances, the processor 102 may normalize the flow rate input value 412 based on a known maximum flow rate of the PD fluid using the PD fluid pump 70. Graph 650 of FIG. 6 shows an example of flow rates of PD fluid in relation to the output signals 312 from the motor driver 108.

The processor 102 then applies the inputs 402 to 410, 412, and/or 414 to the machine learning algorithm 320 of FIG. 4 (block 512). The processor 102 may also apply the inputs 412 and/or 414 to the machine learning algorithm 320. The machine learning algorithm 320 is configured to output an estimated PD fluid pressure 416 of PD fluid within the patient line 28 (block 512). The processor 102 may store the estimated PD fluid pressure 416 to a log file stored in the memory 104. The processor 102 may also cause the estimated PD fluid pressure 416 to be displayed by the user interface 110 of the PD machine 20.

In some embodiments, the processor 120 compares the estimated PD fluid pressure 416 to a threshold or range (block 514). The threshold may be, for example, 300 kilopascal ("kPa") (43.5 psig), 400 kPa (58.0 psig), 500 kPa (72.5 psig), etc., which is indicative of an occlusion, full peritoneal cavity, and/or a partially (or fully) blocked catheter, patient line 28, or filter 40. The range may be from 40 kPa (5.8 psig) to 300 kPa (43.5 psig), for example. In some embodiments, the processor 102 averages the estimated PD fluid pressures 416 over a short time duration (e.g., applies a smoothing function), such as one second, two seconds, etc., to smooth positive and negative pressure spikes from the pump strokes of the PD fluid pump 70. The processor 102 may then compare the smoothed, estimated pressure 416 to the threshold and/or range.

When the estimated pressure 416 exceeds the threshold and/or is outside of the specified range, the processor 102 is configured to cause the motor driver 108 to stop the motor 308 and/or generate an alert/alarm 515 (block 516). In some embodiments, the processor 102 may also display the alert/alarm on the user interface 110 of the PD machine 20. To cause the motor driver 108 to stop, the processor 102 may stop sending input signals 310 and/or transmit an input signal 310 that specifies actuation of the motor 308 is to be halted. When the estimated pressure 416 does not exceed the threshold and/or is within the range, the processor 102 determines if an instruction is received to stop the PD fluid pump 70, such as at the end of a PD fill phase or the end of a PD treatment (block 518). If the PD fluid pump 70 is to continue pumping, the procedure 500 returns to block 504 where the processor 102 transmits an input signal 310 to the driver motor 108 to cause the motor 308 to keep operating. When an instruction to stop the PD fluid pump is received, the processor 102 causes the motor driver 108 to stop by either refraining from transmitting input signals or sending an input signal to halt the motor 308 (block 520). The example procedure then ends.

Machine Learning Algorithm Training Embodiment

The example machine learning algorithm 320 is trained prior to use on the PD machine 20. As shown in FIG. 3, in some embodiments, the PD system 10 may also include a training server 330 that is configured to train the machine learning algorithm 320. The training server 330 is configured to receive the inputs 402 to 410 (e.g., characteristics) that are related to the output signals 312, the flow rate input 412, and/or the upstream pressure input 414 in conjunction with a known PD fluid pressure within the patient line 28. As shown in FIG. 4, for training, known PD fluid pressures 418 are input into the machine learning model 320 in combination with the inputs 402 to 414 discussed above. The correlation between the inputs 402 and/or 414 and the known PD fluid pressures 418 is processed using, for example, a Gaussian process regression, a linear regression, a logic regression, a decision tree, a gradient boosting algorithm, a random forest algorithm, a k-nearest neighbor algorithm, a k-means algorithm, a support-vector machine, a Naïve Bayes algorithm or combinations thereof. The training is designed to determine (weighted) relationships between the inputs and the known fluid pressures 418.

The training is performed on a dataset that may be obtained from a plurality of cyclers 20 of the same (or similar model and/or type) as the PD machine 20 used for patient PD treatments. The known PD fluid pressure 418 is obtained from a pressure sensor that is placed downstream of the PD fluid pump 70 on the patient line 28 (or between the patient line 28 and the disposable filter set 40). The patient lines used for training may have similar thicknesses and lengths as the patient line 28 used for PD treatments.

Figure 7:
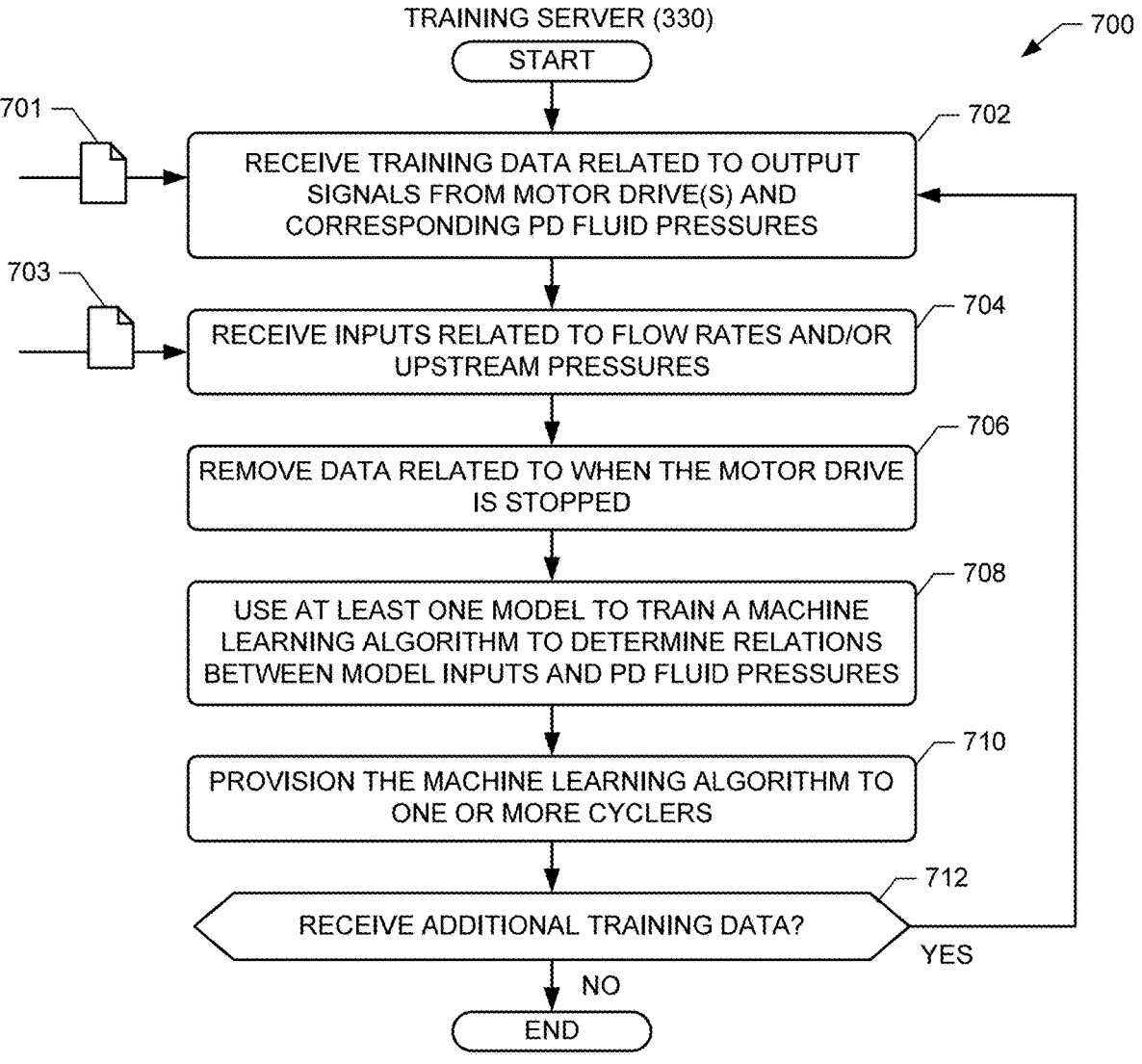
FIG. 7 shows a flow diagram illustrating an example procedure for training the machine learning model of FIG. 4, according to an example embodiment of the present disclosure.

FIG. 7 shows a flow diagram illustrating an example procedure 700 for training the machine learning model 320 of FIG. 4, according to an example embodiment of the present disclosure. The example procedure 700 may be carried out by, for example, the training server 330 of FIG. 3. Although the procedure 700 is described with reference to the flow diagram illustrated in FIG. 7, it should be appreciated that many other methods of performing the functions associated with the procedure 700 may be used. For example, the order of many of the blocks may be changed based on a number of machine learning algorithms and inputs used, certain blocks may be combined with other blocks, and many of the blocks described are optional.

The example procedure 700 begins when the training server 330 receives a training data set 701 that includes at least some of the characteristics (e.g., the inputs 402 to 410) of output signals 312 from motor derivers 108 indicative of motor load during activation of PD fluid pumps (block 702). The characteristics are correlated with a measured PD fluid pressure 418 at a time the output signal 312 is generated by the motor driver 108. The training data set 701 may be collected from one or more PD machines 20 having the same (or similar) PD fluid pumps. The training data 701 may be sampled from output signals at a rate that is identical or similar to the rate discussed above during use of the filter window 602.

Figure 8:
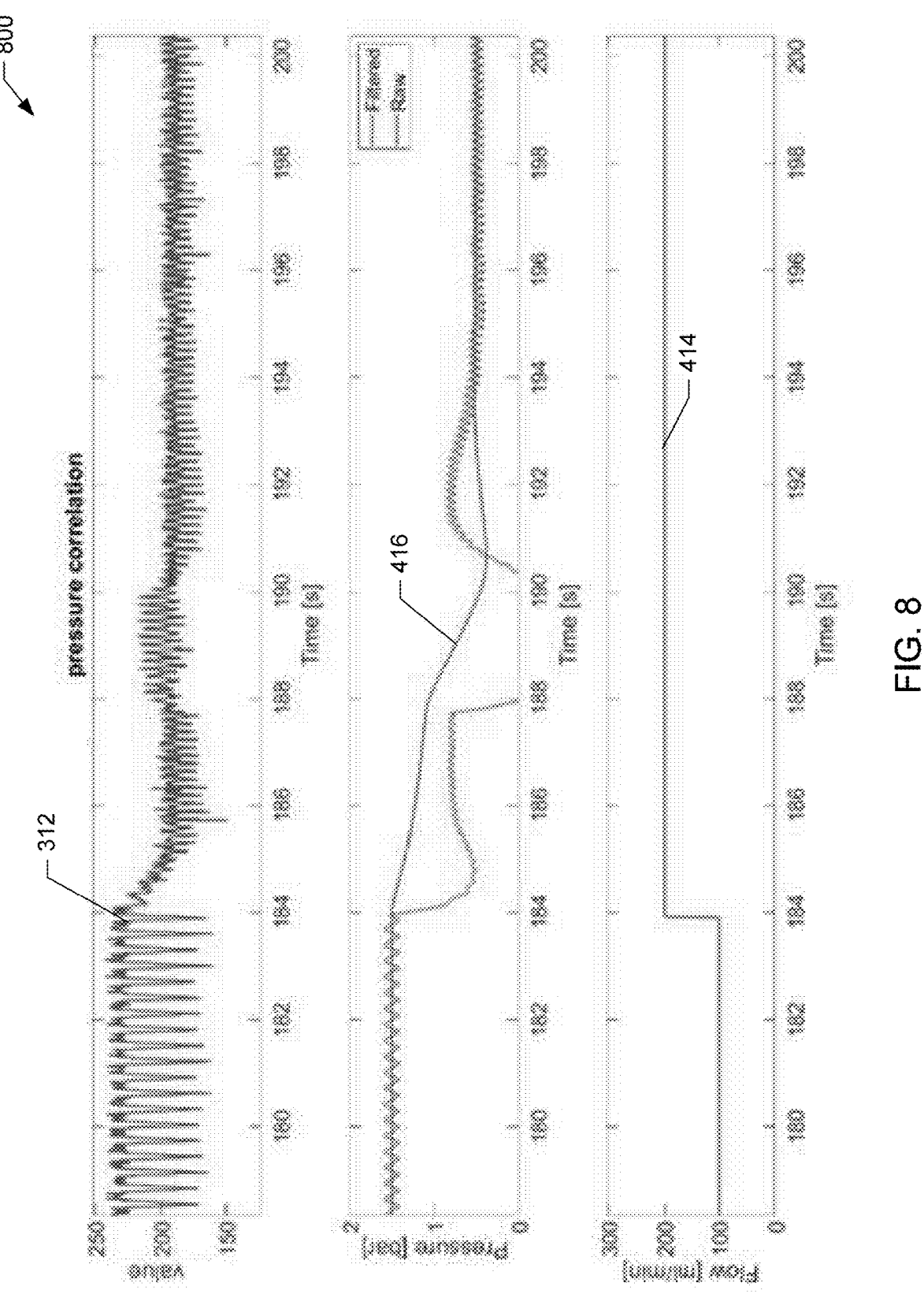
FIG. 8 are graphs that show a correlation with output signals from PD fluid pumps, a flow rate, and a measured PD pressure, which may be included within a training data set for the machine learning algorithm of FIG. 4, according to an example embodiment of the present disclosure.

As shown in FIG. 7, the training server 330 may also receive a training data set 703 that correlates a flow rate and/or upstream pressure with the known PD fluid pressure 418 (block 704). FIG. 8 is a diagram of graphs 800 that show a correlation with output signals 312 from PD fluid pumps 70, a flow rate 414, and a measured PD pressure 418, which may be included within the training data sets 701 and 703, according to an example embodiment of the present disclosure. The flow rate 414 may be measured from the sensor 322 of FIG. 3 or determined based on operational parameters for performing a PD treatment. FIG. 8 also shows that the known PD fluid pressure 418 may be filtered or smoothed using a smoothing function to remove ripples from pump strokes. In the illustrated example of FIG. 8, there is a strong correlation between values of output signals and pressure when the flow rate changes from 100 millimeters ("ml") per minute to 200 ml/minute.

Returning to FIG. 7, the training server 330 may remove training data that corresponds to when the PD fluid pumps are stopped (block 706). This data may be indicated by a flow rate of 0 ml/minute. The training server 330 next uses at least one machine learning model to determine relations, correlations, and correspondences between the inputs 402 to 414 and the known, measured PD fluid pressures 418 (block 708). The training server 330 may determine weights and/or whether some inputs are not correlated with PD fluid pressure.

The training server 330 may then use another data set to validate the machine learning algorithm 320. For validation, the training server 330 uses training data that is associated with known PD fluid pressures 418. However, the training server 330 uses the inputs 402 to 414 to estimate the PD fluid pressure 416. The training server 330 then compares the estimated PD fluid pressure 416 with the measured PD fluid pressure 418 to determine an accuracy of the machine learning model 320.

Figure 9:
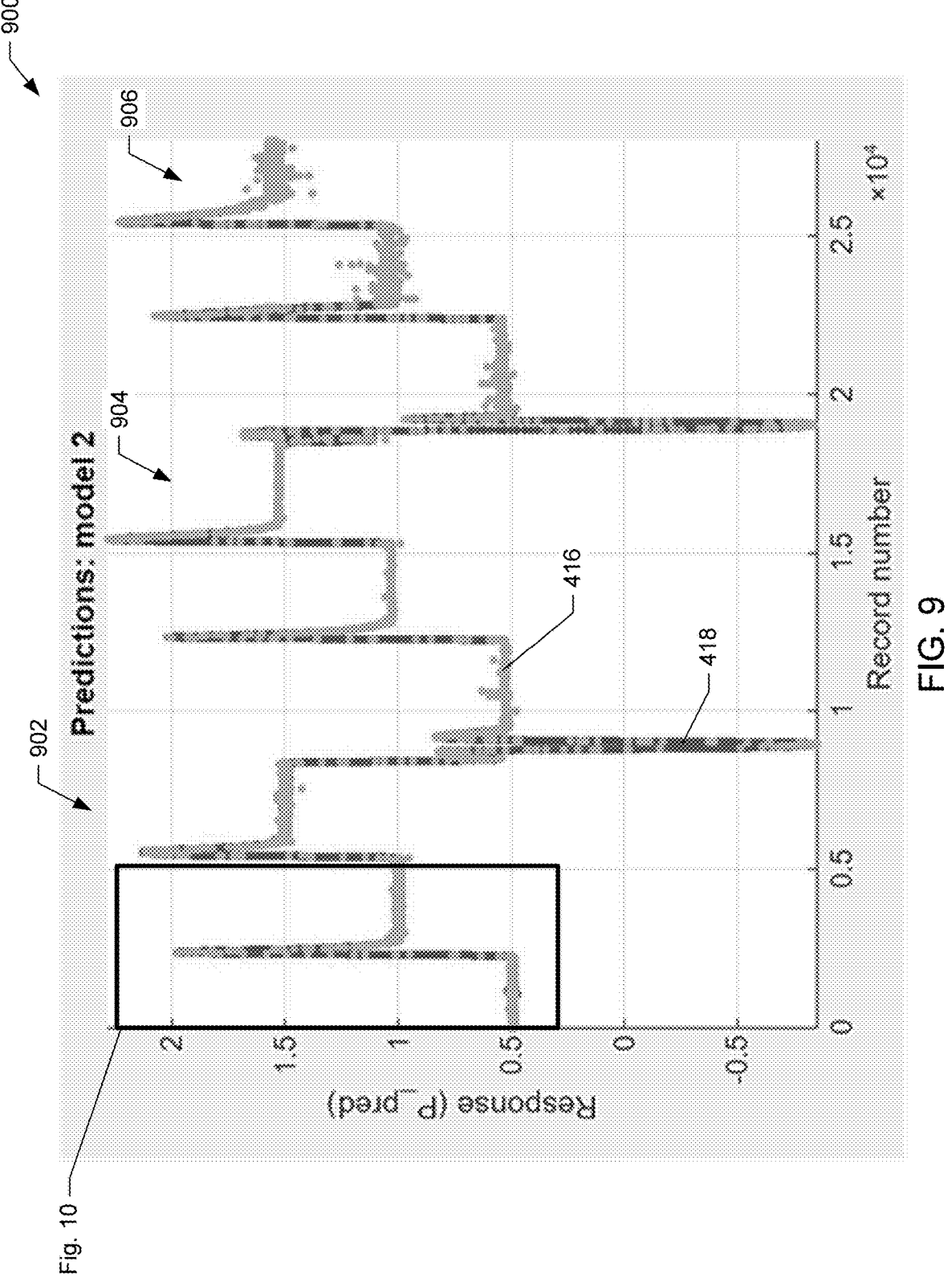
FIGS. 9 and 10 are graphs that illustrate an accuracy of the machine learning model, according to an example embodiment of the present disclosure.
Figure 10:
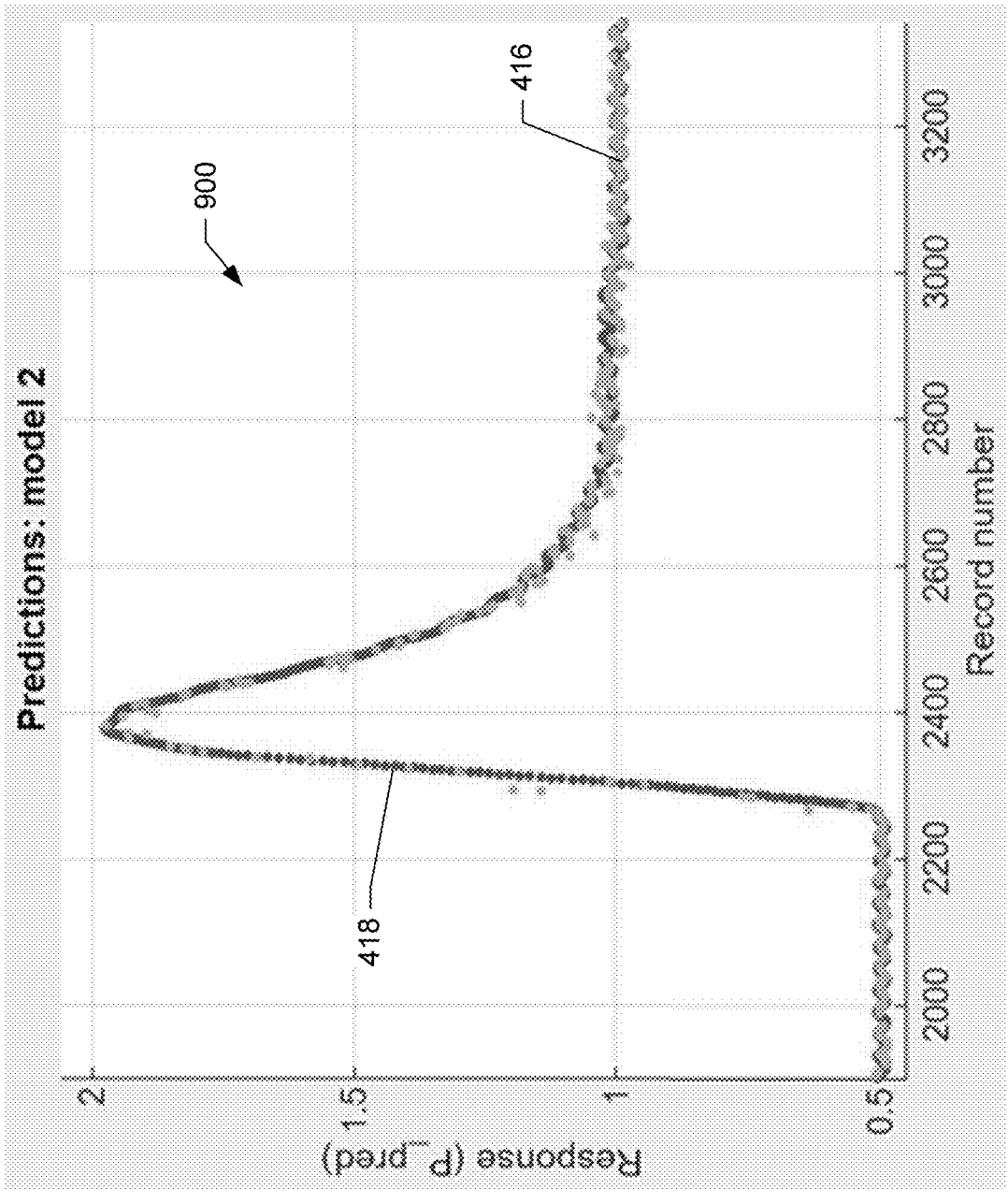

FIG. 9 is a diagram of a graph 900 that illustrates the accuracy of the machine learning model 320, according to an example embodiment of the present disclosure. The graph 900 shows the pressure of the PD fluid at 0.5 bar, 1 bar, and 1.5 bar at three separate flow rates. For example, the pressure at a first set 902 was at a flow rate of 100 ml/min, the pressure at a second set 904 was at a flow rate of 200 ml/min, and the pressure at a third set 906 was at a flow rate of 300 ml/min. A first shade of data shows the estimated PD fluid pressure 416. A second shade of data shows the measured, actual PD fluid pressure 418 in a patient line. The graph 900 shows that the estimated PD fluid pressure 416 is almost identical to the measured pressure 418. FIG. 10 shows an enlarged area of the graph 900 showing the accuracy of the estimated PD fluid pressure. While the data in FIGS. 9 and 10 shows a slight phase shift in the data due to the filter window 602, the time delta is negligible for the purposes of estimating PD fluid in the patient line 28 of the PD machine 20.

Returning to FIG. 7, after the machine learning model 320 is trained, the training server 330 is configured to provision the machine learning model 320 on one or more cyclers 20 (block 710). This may include transmitting the machine learning model 320 over a network to the PD machine 20 for storage in the memory 104. Alternatively, the machine learning model 320 is installed on the PD machine 20 at a time of manufacture.

Periodically, the training server 330 determines if additional training data is available (block 712). If no additional training data is available, the example procedure 700 ends. However, when there is additional training data, the procedure 700 returns to block 702 to update the machine learning model 320 based on the new data. The training server 330 may then transmit the updated machine learning model 320 to the cyclers 20 via a network, for example.

PD Fluid Pump Diagnostic Embodiment

In some embodiments, the downstream pressure sensor of the PD machine 20 may be retained. However, the processor 102 may still use the machine learning algorithm 320 as a diagnostic check of the PD fluid pump 70. The processor 102 is configured to compare the estimated PD fluid pressure 416 based on the output signals 312 from the motor driver 108 to a PD fluid pressure 418 measured by the pressure sensor. When the deviation exceeds a threshold, this may be indicative that a non-dynamic load on the PD fluid pump 70 has changed. As a result, the processor 102 may cause the user interface 110 to display a message indicative that the PD fluid pump 70 should be replaced or serviced. When the deviation is significant, (such as 0.5 bar), the processor 102 may prevent PD treatments to be performed until the PD fluid pump 70 is replaced/serviced.

Conclusion

It will be appreciated that all of the disclosed methods and procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

For example, PD system 10 does not have to use redundant or durable components, and may instead employ a disposable set having a disposable pumping portion that contacts the corresponding medical fluid. In another example, while disposable filter set 40 would not be needed as a last chance filter for a system not having heat disinfection, disposable filter set 40 may still be provided if the fresh PD fluid is made online at the time of use as a last chance filter for the online PD fluid. PD fluid pumping with the disposable set may be performed alternatively via pneumatic pump actuation of a sheet of a disposable cassette of the disposable set, via electromechanical pump actuation of a sheet of a disposable cassette of the disposable set, or via peristaltic pump actuation of a pumping tube segment provided with the disposable set. In a further example, while the pump motor 308 is illustrated as actuating a piston 306, the system 10 may be applied to the pump motor 308 actuating other types of pump actuators for PD fluid pump 70, such as peristaltic pump actuators, centrifugal pump actuators, gear pump actuators, and the like. Moreover, while the pump motor 308 is described as being a stepper motor, the system 10 may be applied to other types of pump motors, such as AC or DC brushed or brushless motors, servo motors, and the like It should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. A peritoneal dialysis ("PD") system comprising:
   a housing;
   a PD fluid pump housed by the housing, the PD fluid pump including an actuator that is actuated by a motor;
   a patient line fluidly coupling the PD fluid pump to a transfer set that is connected to an indwelling catheter leading into a peritoneal cavity of a patient;
   a motor driver configured to control the motor and transmit an output signal that is indicative of a load on the motor;
   a memory storing a machine learning algorithm that associates data related to output signals from motor drivers with known PD fluid pressures within patient lines;
   a processor electrically coupled to the motor driver and the memory, the processor configured to:
   transmit an input signal to activate the motor driver,
   receive the output signal from the motor driver,
   estimate a PD fluid pressure within the patient line by applying data from the received output signal to the machine learning algorithm, and
   cause the motor driver to stop when the estimated PD fluid pressure is above a threshold value.

2. The PD system of claim 1, wherein the processor is further configured to:
   receive a plurality of output signals from the motor driver;
   sample the plurality of output signals at a specified rate using a moving window filter; and
   apply the machine learning algorithm to the data from the sampled plurality of output signals that are within the moving window filter.

3. The PD system of claim 2, wherein the specified rate is between 50 Hz and 1000 Hz for sampling between 1 and 100 output signals within the moving window filter.

4. The PD system of claim 2, wherein the processor is further configured to determine at least one of the following input variable values as the data from the sampled plurality of output signals: (i) a minimum output signal value, (ii) a maximum output signal value, (iii) an average output signal value, (iv) a median output signal value, or (v) a difference of the maximum output signal value and the minimum output signal value; and
   use the at least one of the (i) to (v) for applying the machine learning algorithm to the sampled plurality of output signals that are within the moving window filter.

5. The PD system of claim 4, wherein the processor is further configured to:
   determine or receive an indication of a flow rate of a PD fluid; and
   use the flow rate of the PD fluid in conjunction with the at least one of the (i) to (v) for applying the machine learning algorithm to the sampled plurality of output signals that are within the moving window filter.

6. The PD system of claim 5, wherein the processor is further configured to:
   normalize the flow rate of the PD fluid by dividing the flow rate of the PD fluid by a maximum flow rate; and
   use the normalized flow rate of the PD fluid in conjunction with the at least one of the (i) to (v) for applying the machine learning algorithm to the sampled plurality of output signals that are within the moving window filter.

7. The PD system of claim 5, wherein the processor is configured to receive the flow rate of the PD fluid from a flow rate sensor that is fluidly coupled to the patient line or determine the flow rate of the PD fluid from a programmed PD fluid flow rate.

8. The PD system of claim 5, wherein the machine learning algorithm includes the following input variables as inputs:

at least one of the flow rate of the PD fluid or a normalized fluid flow rate of the PD fluid; and at least one of (i) a minimum output signal value, (ii) a maximum output signal value, (iii) an average output signal value, (iv) a median output signal value, or (v) a difference of the maximum output signal value and the minimum output signal value.

9. The PD system of claim 8, wherein the machine learning algorithm additionally includes an upstream PD fluid pressure as an input variable.

10. The PD system of claim 8, wherein the machine learning algorithm is trained using a data set that associates at least one of the flow rate of the PD fluid or the normalized fluid flow rate of the PD fluid and the at least one of (i) to (v) with a PD fluid pressure within the patient line that is measured by a pressure sensor.

11. The PD system of claim 4, wherein the processor is further configured to:

receive an indication of an upstream PD fluid pressure from a pressure sensor that is located upstream from the PD fluid pump; and use the upstream PD fluid pressure in conjunction with the at least one of the (i) to (v) for applying the machine learning algorithm to the sampled plurality of output signals that are within the moving window filter.

12. The PD system of claim 11, wherein the upstream PD fluid pressure corresponds to a head height pressure.

13. The PD system of claim 1, further comprising a filter set including a hydrophilic filter membrane fluidly coupled between the patient line and the transfer set, wherein the patient line is a dual lumen patient line including a fresh PD fluid lumen and a used PD fluid lumen, and wherein the processor is configured to estimate the PD fluid pressure within the fresh PD fluid lumen.

14. The PD system of claim 1, wherein the motor is a stepper motor and the output signal represents a load angle of the stepper motor.

15. The PD system of claim 1, wherein the processor is further configured to apply a smoothing function to a sequence or stream of the estimated PD fluid pressures.

16. The PD system of claim 1, wherein the actuator includes a piston actuated by the motor.

17. A peritoneal dialysis ("PD") method to estimate PD fluid pressure, the method comprising:

storing in a memory of a PD machine, a machine learning algorithm that associates data related to output signals from motor drivers with known PD fluid pressures within patient lines;

transmitting from a processor of the PD machine to a motor driver of a PD fluid pump, an input signal to activate the motor driver, which causes a motor to actuate an actuator for pumping PD fluid at a specified rate from the PD fluid pump to a patient line that is fluidly coupled to a transfer set that is connected to an indwelling catheter leading into a patient's peritoneal cavity;

receiving, in the processor, output signals from the motor driver that are indicative of a load estimation output of the motor;

estimating, via the processor using the machine learning algorithm, a PD fluid pressure within the patient line based on data related to the received output signals; and causing, via the processor, a user interface of the PD machine to display the estimated PD fluid pressure.

18. The method of claim 17, further comprising causing, via the processor, the motor driver to stop when the estimated PD fluid pressure is above a threshold value out outside of a specified range.

19. The method of claim 17, wherein the machine learning algorithm includes at least one of a Gaussian process regression, a linear regression, a logic regression, a decision tree, a gradient boosting algorithm, a random forest algorithm, a k-nearest neighbor algorithm, a k-means algorithm, a support-vector machine, a Naïve Bayes algorithm or combinations thereof.

20. The method of claim 17, further comprising:

sampling, via the processor, the output signals at a specified rate using a moving window filter; and applying, via the processor, the machine learning algorithm to data from the sampled plurality of output signals that are within the moving window filter.

21. The method of claim 20, wherein the specified rate is between 50 Hz and 1000 Hz for sampling between 1 and 100 output signals within the moving window filter.

22. The method of claim 20, further comprising:

determining, via the processor, at least one of the following input variable values as the data from the sampled output signals: (i) a minimum output signal value, (ii) a maximum output signal value, (iii) an average output signal value, (iv) a median output signal value, or (v) a difference of the maximum output signal value and the minimum output signal value; and using, via the processor, the at least one of the (i) to (v) for applying the machine learning algorithm to the sampled plurality of output signals that are within the moving window filter.

23. The method of claim 22, further comprising:

determining or receiving, via the processor, an indication of a flow rate of the PD fluid; and using, via the processor, the flow rate of the PD fluid in conjunction with the at least one of the (i) to (v) for applying the machine learning algorithm to the sampled plurality of output signals that are within the moving window filter.

24. The method of claim 22, further comprising training the machine learning algorithm using a data set that associates at least one of a flow rate of the PD fluid or a normalized fluid flow rate of the PD fluid and the at least one of (i) to (v) with a PD fluid pressure within the patient line that is measured by a pressure sensor.

* * * * *